US006391346B1

(12) United States Patent
Newmark et al.

(10) Patent No.: US 6,391,346 B1
(45) Date of Patent: May 21, 2002

(54) ANTI-INFLAMMATORY, SLEEP-PROMOTING HERBAL COMPOSITION AND METHOD OF USE

(76) Inventors: Thomas Newmark, 704 Cordell Ct., St. Louis, MO (US) 63132; Paul Schulick, 222 Kipling Rd., Brattleboro, VT (US) 05301

( * ) Notice: Subject to any disclaimer, the term of this patent is extended or adjusted under 35 U.S.C. 154(b) by 0 days.

(21) Appl. No.: 09/825,837

(22) Filed: Apr. 5, 2001

(51) Int. Cl.⁷ ............................................. A61K 35/78
(52) U.S. Cl. ...................... 424/756; 424/733; 424/741
(58) Field of Search .............................. 424/733, 756, 424/741

(56) References Cited

U.S. PATENT DOCUMENTS

| 5,494,668 A | 2/1996 | Patwardhan |
|---|---|---|
| 5,683,698 A | 11/1997 | Chavali et al. |
| 5,854,291 A | 12/1998 | Laughlin et al. |
| 5,910,307 A | 6/1999 | Kwak et al. |
| 5,916,565 A | 6/1999 | Rose et al. |

*Primary Examiner*—Christopher R. Tate
*Assistant Examiner*—Randall Winston
(74) *Attorney, Agent, or Firm*—Patton Bogg LLP

(57) ABSTRACT

An orally administered composition capable of reducing inflammation in animals, preferably humans, while promoting sleep for such animals, contains a therapeutically effective amount of a post-supercritical carbon dioxide hydroalcoholic extract of ginger, therapeutically effective amounts of supercritical carbon dioxide extracts of hops, chamomile, ginger, valerian and melissa; and therapeutically effective amounts of hydroalcoholic extracts of holy basil, turmeric, scutellaria baicalensis, chamomile and hops. The composition is preferably orally administered on a daily basis for at least about 4 weeks.

37 Claims, No Drawings

ANTI-INFLAMMATORY, SLEEP-PROMOTING HERBAL COMPOSITION AND METHOD OF USE

BACKGROUND OF THE INVENTION

This invention relates to herbal compositions. More particularly, this invention relates to an herbal composition capable of reducing inflammation in bones and joints in animals, particularly humans, while promoting safe and restful sleep. The present invention further relates to methods of using such herbal composition to reduce inflammation in bones and joints in animals, particularly humans, while promoting safe and restful sleep.

Arthritic disorders, including rheumatism, osteoarthritis, dysplasia, lupus, bursitis, and gout, are all characterized by inflammation and pain in bones, joints, muscles, and related connective tissues. Most of the forms are progressive. Bone and joint inflammation is a scourge of both animals and humans. Those who suffer from inflammation experience pain and discomfort and may, in advanced cases, lose the effective use of inflamed joints. Thus, the goal of therapeutic methods for treating bone or joint inflammation is the relief of pain and discomfort and the restoration of use of inflamed joints.

Natural ingredients, e.g., herbs, have been used to treat bone and joint inflammation, especially in eastern countries, and, increasingly, in western countries. Compositions composed of natural ingredients and said to be useful in reducing inflammation are disclosed, e.g., in U.S. Pat. Nos. 5,494,668; 5,683,698; 5,916,565; 5,854,291; and 5,910,307.

U.S. Pat. No. 5,494,668 (Patwardhan) discloses a method of treating degenerative musculoskeletal diseases such as rheumatoid arthritis and osteoarthritis in an animal, typically a human, involving administering (typically enterally) to the animal beneficiated extracts of the ashwagandha, sallai Guggul, turmeric, and ginger plants, in a predetermined proportion relative to each other with or without other biologically active inorganic ingredients.

U.S. Pat. No. 5,683,698 (Chavali et al.) discloses an orally administered herbal formulation for reducing or alleviating symptoms associated with rheumatoid arthritis, osteoarthritis, and reactive arthritis and for reducing the production of pro-inflammatory cytokines, wherein the formulation contains herbal extracts taken from Alpinia, Smilax, Tinospora, Tribulus, Withania, and Zingiber plants.

U.S. Pat. No. 5,916,565 (Rose et al.) discloses an orally administered composition for prophylaxis and therapy of joint and connective tissue disorders in vertebrates, wherein the composition contains metabolic precursors, herbal phytochemicals, and palatability agents. Specific herbal phytochemicals disclosed include cayenne, ginger, turmeric, yucca, Devil's claw, nettle leaf, Black Cohosh, alfalfa and celery seeds.

U.S. Pat. No. 5,854,291 (Laughlin, et al.) discloses a topically-applied pain reliever composition for treating such discomforts as arthritis pain, the composition being composed of capsaicin and, optionally, a plant extract selected from the group consisting of nettle extract, yarrow extract, coltsfoot extract, birch extract, rosemary extract, horsetail extract, ginger extract, chamomile extract, comfrey extract, lavender extract, and bergamot extract.

U.S. Pat. No. 5,910,307 (Kwak, et al.) discloses a combined medicinal plant composition for alleviating acute/chronic inflammation, composed of Clematis Radix, Trichosanthes root, and Prunella Herba (which contains oleanolic acid ursolic acid) in a certain ratio.

Certain enzymes appear to play a role in causing inflammation. One of the features of inflammation is increased oxygenation of arachidonic acid which is metabolized by two enzymic pathways—the cyclooxygenase (CO) and the 5-lipoxygenase (5-LO) pathways—leading to the production of prostaglandins and leukotrienes, respectively. Prostaglandins and leukotrienes are mediators of inflammation. Therapies designed to inhibit cydooxygenase and/or lipoxygenase activity are therefore of great interest.

There are two forms of the cyclooxygenase enzyme: cyclooxygenase-1 (COX-1) and cyclooxygenase-2 (COX-2). The latter form, i.e., COX-2, appears to play a key role in inflammatory processes. Recent scientific studies suggest that inhibiting the COX-2 enzyme may be an effective way to reduce inflammation without the side effects associated with irreversible COX-1 inhibition. In addition, recent scientific studies also suggest that COX-2 inhibition may serve an important function in promoting normal cell growth in the colon, pancreas, breast tissue and other organ systems.

Drugs are being developed which are intended to selectively inhibit COX-2 with minimal effect on COX-1. However, despite the emphasis on COX-2 inhibition, these drugs appear to have serious side effects, e.g., a breakdown in digestive protective mucus and prevention of normal healing processes. For example, non-steroidal anti-inflammatory drugs (NSAIDS) can have a variety of toxic side effects such as, e.g., gastric erosion and adverse effects on kidneys and liver, and may inadequately regulate the cellular immune functions and secretions of various cytokines.

Several herbs have been found to inhibit the COX-2 enzyme.

For example, holy basil has been found to possess significant anti-inflammatory properties and is capable of blocking both the cyclooxygenase and lipoxygenase pathways of arachidonate metabolism. Ursolic acid and oleanolic acid (less active), the marker constituents of holy basil, have been found to a significant COX-2 inhibitory effect.

Shogaol, a pungent component of ginger, has been found to inhibit cyclooxygenase. Eugenol, another constituent of ginger, has also been found to be a 5-lipoxygenase inhibitor and to possess potent anti-inflammatory and/or anti-rheumatic properties.

Scutellaria baicalensis also has been found to inhibit the COX-2 enzyme.

According to the USDA database, green tea contains six constituents having cyclooxygenase-inhibitor activity. According to the Napralert database, green tea contains fifty one constituents having anti-inflammatory activity. The polyphenols in green tea were found to cause a marked reduction in cyclooxygenase-2. Flavan-3-ol derivatives (+)-catechin, also present in green tea, have been reported to be COX-1 and COX-2 inhibitors. In addition, salicylic acid, another constituent of green tea, also has been found to be a COX-2 inhibitor.

Berberine, found in barberry and Chinese goldthread, has been found to inhibit COX-2 without inhibiting COX-1 activity.

Inflammation is also mediated by oxygen-derived free radicals. Free radicals degrade hyaluronic acid, modify collagen and perhaps proteoglycan structure and/or synthesis, alter and interact with immunoglobulins, activate degradative enzymes and inactivate their inhibitors, and possibly participate in chemotaxis. It is desirable to scavenge and detoxify free radicals before they reach the affected area.

Herbs which can scavenge free radicals include, e.g., holy basil, turmeric, and scutellaria baicalensis.

Although herbs having anti-inflammatory and antioxidant properties are known, it is continually desirable to provide anti-inflammatory/antioxidant herbal compositions which also promote safe and restful sleep for those which wish to take anti-inflammatory compositions at night.

Although having both anti-inflammatory and antioxidant properties, green tea, barberry and Chinese goldthread also tend to be slightly stimulating. Thus, anti-inflammatory and/or antioxidant compositions containing these herbs should not be taken at night as they can interfere with sleep.

Melissa and valerian are known to provide optimal sleep quality and are each a source of anti-inflammatory compounds. However, it is still desirable to provide compositions having improved anti-inflammatory and sleep-promoting benefits than would be obtained with compositions containing either melissa or valerian alone.

Accordingly, a primary object of this invention is to provide an orally administered herbal composition capable of effectively reducing bone and joint inflammation in animals, particularly humans, while promoting safe and restful sleep.

A further object of this invention is to provide the herbal composition set forth in the preceding object, wherein the composition reduces said inflammation by inhibiting COX-2.

Another object of this invention is to provide the herbal composition set forth in the preceding objects, wherein the composition is capable of reducing inflammation while avoiding the side effects associated with traditional drug therapy.

A further object of this invention is to provide the herbal composition set forth in the preceding objects, wherein the composition also has antioxidant properties.

A still further object of this invention is to provide the herbal composition described in the preceding objects, wherein the composition is composed of herbal extracts that are prepared without chemical solvents.

Yet another object of this invention is to provide a method of reducing inflammation in animals (particularly humans) using an herbal composition having the properties set forth in the preceding objects.

These objects and others are achieved in the present invention.

SUMMARY OF THE INVENTION

The present invention is based on the discovery that a combination of certain herbs properly extracted and blended in appropriate proportions can not only provide anti-inflammatory and antioxidant benefits, but can also promote deep and satisfying sleep.

Accordingly, one aspect of the present invention is directed to an orally administered herbal composition capable of reducing inflammation in animals, preferably humans, afflicted with inflammation, and further capable of promoting sleep for such animals, the composition being composed of a therapeutically effective amount of a post-supercritical carbon dioxide hydroalcoholic extract of ginger; therapeutically effective amounts of supercritical carbon dioxide extracts of hops, chamomile, ginger (preferably certified organic ginger), valerian and melissa; and therapeutically effective amounts of hydroalcoholic extracts of holy basil, turmeric, scutellaria baicalensis, chamomile and hops.

A second aspect of the present invention is directed to a method for reducing inflammation in animals, preferably humans, suffering from inflammation while promoting sleep for such animals, the method involving the steps of:
 (1) providing the composition of this invention; and
 (2) orally administering the composition to the animal in an amount and for a time period effective to reduce inflammation in the animal.

The composition of this invention reduces inflammation by inhibiting COX-2. As a result, the composition not only reduces inflammation but also promotes healthy joint function and normal cell growth.

In addition, the composition of this invention is capable of scavenging toxic active oxygen species, thereby providing antioxidant benefits.

The composition of this invention also safely promotes restful sleep and, thus, can be used at night. This characteristic of the composition is due to the presence of hops, chamomile, melissa and valerian, which are sedating agents that do not interfere with the anti-inflammatory or antioxidant properties of the composition.

Another benefit provided by the composition of this invention is that it can be prepared without the use of chemical solvents. This feature is achieved by using a supercritical solvent-free extraction process to obtain the extracts. Such extraction process allows for the highest potency of active compounds in the extracts, as much as 250 times the potency of the original fresh plant material.

DETAILED DESCRIPTION OF THE INVENTION

As stated above, the present invention provides an orally administered herbal composition and a method of using the composition to reduce inflammation in animals, preferably humans, suffering from inflammation, while also promoting sleep for such animals.

The composition of this invention is composed of: a post-supercritical carbon dioxide hydroalcoholic extract of ginger, supercritical carbon dioxide extracts of hops, chamomile, ginger (preferably certified organic ginger), valerian and melissa; and hydroalcoholic extracts of holy basil, turmeric, scutellaria baicalensis, chamomile and hops.

The composition of this invention will contain "therapeutically effective amounts" of the herbal extracts recited above. As used herein with respect to the extracts of ginger, holy basil, turmeric and scutellaria baicalensis, the term "therapeutically effective amount" refers to that amount of the extract which will contribute to the inflammation-reducing ability of the composition. With respect to the extracts of melissa, valerian, hops and chamomile, the term "therapeutically effective amount" means that amount of the herb which will promote sleep without interfering with the composition's anti-inflammatory properties. Preferably, the composition of this invention contains:
 (A) from about 7% to about 11%, more preferably from about 8% to about 10%, by weight of the post-supercritical carbon dioxide hydroalcoholic extract of ginger;
 (B) from about 1% to about 3%, more preferably from about 1.5% to about 2.5%, by weight of the supercritical carbon dioxide extract of ginger;
 (C) from about 5.5% to about 8.5%, more preferably from about 6% to about 8%, by weight of the supercritical carbon dioxide extract of chamomile;
 (D) from about 5.5% to about 8.5%, more preferably from about 6% to about 8%, by weight of the supercritical carbon dioxide extract of hops;

(E) from about 18% to about 26%, more preferably from about 20% to about 24%, by weight of the hydroalcoholic extract of holy basil;

(F) from about 2.0% to about 4.0%, more preferably from about 2.5% to about 3.5%, by weight of the supercritical carbon dioxide extract of valerian;

(G) from about 10% to about 16%, more preferably from about 11% to about 15%, by weight of the supercritical carbon dioxide extract of melissa (lemon balm);

(H) from about 12% to about 18%, more preferably from about 13% to about 17%, by weight of the hydroalcoholic extract of turmeric;

(I) from about 12% to about 18%, more preferably from about 13% to about 17%, by weight of the hydroalcoholic extract of scutellaria baicalensis;

(J) from about 2.5% to about 4.5%, more preferably from about 3% to about 4%, by weight of the hydroalcoholic extract of chamomile; and (K) from about 2.5% to about 4.5%, more preferably from about 3% to about 4%, by weight of the hydroalcoholic extract of hops.

The post-supercritical carbon dioxide hydroalcoholic extract of ginger used in the present invention is preferably prepared as follows. The ginger rhizome, which is preferably cryogenically ground to preserve heat sensitive components, is subjected to supercritical carbon dioxide extraction to obtain: (i) an oil extract (referred to herein as "the supercritical carbon dioxide extract" of ginger) containing delicate lipophilic (oil-soluble/non-polar) components, and (ii) an oil-free residue. The oil-free residue is then extracted in a water/alcohol (preferably water/ethanol) mixture (composed of 60–80 parts alcohol and 40–20 parts water). The alcohol/water liquid is then evaporated off, leaving a powdered extract residue, referred to herein as "the post-supercritical carbon dioxide hydroalcoholic extract" of ginger.

The composition of this invention will preferably contain the post-supercritical carbon dioxide hydroalcoholic extract and the supercritical carbon dioxide extract of ginger at a weight ratio of from about 4 to about 5 parts post-supercritical carbon dioxide hydroalcoholic extract per 1 part supercritical carbon dioxide extract. More preferably, the composition will contain about 4.5 parts post-supercritical carbon dioxide hydroalcoholic extract of ginger per 1 part of the supercritical carbon dioxide extract of ginger.

The supercritical carbon dioxide extracts of ginger, chamomile, hops, valerian and melissa can be prepared according to known supercritical carbon dioxide extraction methods, such as disclosed, e.g., in E. Stahl, K. W. Quirin, D. Gerard, Dense Gases for Extraction and Refining, Springer Verlag 1988, which is hereby incorporated by reference herein.

The hydroalcoholic extracts of holy basil, turmeric, scutellaria baicalensis, hops and chamomile used in the present invention can be prepared according to conventional hydroalcoholic extraction techniques. For example, the hydroalcoholic extracts can be prepared by extracting the plant portion in a water/alcohol (preferably water/ethanol) mixture (preferably composed of 60–80 parts alcohol and 40–20 parts water), and then evaporating off the water/alcohol liquid, leaving a powdered extract residue (referred to herein as "the hydroalcoholic extract").

In the composition of this invention, the supercritical carbon dioxide extract of chamomile and the hydroalcoholic extract of chamomile will preferably be present at a weight ratio of about 1.75–2.25 parts supercritical carbon dioxide extract per 1 part of hydroalcoholic extract, more preferably about 2.0 parts of supercritical carbon dioxide extract per 1 part of hydroalcoholic extract.

The composition of this invention will preferably contain the supercritical carbon dioxide extract of hops and the hydroalcoholic extract of hops at a weight ratio of about 1.75–2.25 parts supercritical carbon dioxide extract per 1 part of hydroalcoholic extract, more preferably about 2.0 parts of supercritical carbon dioxide extract per 1 part of hydroalcoholic extract.

The post-supercritical carbon dioxide hydroalcoholic extract of ginger used in the present invention will preferably contain from about 2% to about 4%, more preferably about 3%, by weight of pungent compounds (e.g., shogaol).

The supercritical carbon dioxide extract of ginger used in the present invention will preferably contain from about 20% to about 40%, more preferably about 30%, by weight of pungent compounds (e.g., shogaol) and from about 7 to about 9%, more preferably about 8%, by weight of zingiberene.

The supercritical carbon dioxide extract of chamomile used in the present invention will preferably contain at least about 25% by weight of alpha-bisabolol.

The hydroalcoholic extract of chamomile used in this invention will preferably contain at least about 3% by weight of apigeninglycosides.

The supercritical carbon dioxide extract of hops used in the present invention will preferably contain from about 30% to about 40%, more preferably about 35%, by weight of humulones, and from about 9% to about 15%, more preferably about 12%, by weight of lupulones.

The hydroalcoholic extract of hops used in this invention preferably comprises from about 1% to about 2%, more preferably about 1.5%, by weight of xanthohumol.

The supercritical carbon dioxide extract of valerian used in this invention preferably comprises from about 50% to about 70%, more preferably about 60%, by weight of valepotriates.

The supercritical carbon dioxide extract of melissa used in this invention preferably comprises from about 0.5% to about 2%, more preferably about 1%, by weight of essential oil.

The hydroalcoholic extract of holy basil used in this invention preferably comprises from about 1% to about 3%, more preferably about 2%, by weight of ursolic acid.

The hydroalcoholic extract of turmeric used in this invention preferably comprises from about 5% to about 9%, more preferably about 7%, by weight of curcumin.

In preferred embodiments, the composition of this invention further contains a pharmaceutically acceptable carrier. As used herein, the term "pharmaceutically acceptable carrier" is meant to include one or more pharmaceutically suitable, inactive excipients, carriers, diluents, lubricants, adjuvants, and lubricants. Non-limiting examples of inactive excipients, carriers, diluents, lubricants, and adjuvants which can be used in the composition of the present invention include: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glaze, talc, croscarmellose sodium, povidone, water and gelatin. Additional inactive excipients, carriers, diluents, lubricants and adjuvants which may be used with the active-ingredient composition of this invention are disclosed in the Handbook of Food Additives (CRC Press), which is incorporated by reference herein in relevant part.

The pharmaceutically acceptable carrier can be present in any conventional amount used in an orally administered composition.

The present invention also provides a method for reducing inflammation in animals, preferably humans, while also promoting sleep for such animals. The method of this invention involves the steps of: (1) providing the composition of this invention; and (2) orally administering the composition to the animal in an amount and for a time period effective to reduce inflammation in the animal.

The orally administered composition of this invention can be in any conventional form including, e.g., capsules (hard or soft), tablets, elixirs, powders, granules, suspensions in water or non-aqueous media, sachets, etc. Most preferably, the composition is in the form of one or more tablets, pills or capsules.

If in tablet, pill or capsule form, the composition of this invention is preferably orally ingested with a liquid, preferably water, more preferably with about 8 ounces of water.

Preferably, the amount of the composition administered in the method of this invention is that amount sufficient to provide a daily dosage of at least about 500 mg, more preferably from about 700 to about 750 mg, of the herbal extracts. In other words, the daily dosage of the composition of this invention will contain preferably at least about 500 mg, more preferably from about 700 to about 750 mg of the herbal extracts. Inactive ingredients can be present in the composition in amounts conventionally used in orally ingested compositions.

If consumed on a daily basis, the composition of this invention is preferably orally administered for a period of at least about 4 weeks. If the composition is not taken on a daily basis, the effective period of time for reducing inflammation will take longer and will depend on the frequency of consumption and the amount consumed.

Set forth in the Table below is a preferred embodiment of the orally administered composition (excluding inactive ingredients) of this invention. The amounts recited in the Table represent the preferred daily dosage (and one serving) of the ingredients listed.

TABLE

| Ingredient | Amount |
| --- | --- |
| Holy Basil (leaf), extract<br>(2% ursolic acid - 2 mg) | 150 mg |
| Valerian, valeriana officinalis and<br>*Valeriana mexicanus* (root)<br>Supercritical $CO_2$ extract<br>(60% valepotriates - 12 mg) | 20 mg |
| Melissa (leaf)<br>Supercritical $CO_2$ extract<br>(1% essential oil - 0.85 mg)<br>(including neral and geranial) | 85 mg |
| Turmeric (rhizome), extract<br>(7% curcumin - 7 mg) | 100 mg |
| *Scutellaria baicalensis* (root), extract 5:1 | 100 mg |
| Ginger (rhizome),<br>(post-supercritical $CO_2$ ethanolic extract)<br>(3% pungent compounds - 1.8 mg) | 61.5 mg |
| Ginger, certified organic (rhizome)<br>Supercritical $CO_2$ extract,<br>(30% pungent compounds - 4 mg,<br>8% zingiberene - 1 mg) | 13.5 mg |
| Chamomile (flower), supercritical $CO_2$ extract<br>(minimum 25% alpha-bisabolol - 12.5 mg) | 50 mg |
| Hops (strobiles), supercritical $CO_2$ extract<br>(35% humulones - 17 mg)<br>(12% lupulones - 6 mg) | 50 mg |
| Hops (strobiles), ethanolic extract<br>(1.5% xanthohumol - 0.37 mg) | 25 mg |

TABLE-continued

| Ingredient | Amount |
| --- | --- |
| Chamomile (flower), extract<br>(minimum 3% apigeninglycosides - 0.75 mg)<br>Olive Oil, certified organic<br>Yellow Beeswax | 25 mg |

In preferred embodiments of the soft gel capsule form of the present invention, the capsule is composed of gelatin, vegetable glycerin, purified water and carob.

For oral administration of the above-recited formulation, the two soft gel capsules (together constituting one serving) are preferably taken daily, with 8 ounces of water.

What is claimed is:

1. An orally administered composition for reducing inflammation in animals while also promoting sleep for the animals, comprising: a therapeutically effective amount of a post-supercritical carbon dioxide hydroalcoholic extract of ginger; therapeutically effective amounts of supercritical carbon dioxide extracts of hops, chamomile, ginger, valerian and melissa; and therapeutically effective amounts of hydroalcoholic extracts of holy basil, turneric, scutellaria baicalensis, chamomile and hops.

2. A composition according to claim 1, comprising:
   (A) from about 7% to about 11% by weight of the post-supercritical carbon dioxide hydroalcoholic extract of ginger;
   (B) from about 1% to about 3% by weight of the supercritical carbon dioxide extract of ginger;
   (C) from about 5.5% to about 8.5% by weight of the supercritical carbon dioxide extract of chamomile;
   (D) from about 5.5% to about 8.5% by weight of the supercritical carbon dioxide extract of hops;
   (E) from about 18% to about 26% by weight of the hydroalcoholic extract of holy basil;
   (F) from about 2.0% to about 4.0% by weight of the supercritical carbon dioxide extract of valerian;
   (G) from about 10% to about 16% by weight of the supercritical carbon dioxide extract of melissa;
   (H) from about 12% to about 18% by weight of the hydroalcoholic extract of turmeric;
   (I) from about 12% to about 18% by weight of the hydroalcoholic extract of scutellaria baicalensis;
   (J) from about 2.5% to about 4.5% by weight of the hydroalcoholic extract of chamomile; and
   (K) from about 2.5% to about 4.5% by weight of the hydroalcoholic extract of hops.

3. A composition according to claim 1, comprising:
   (A) from about 8% to about 10% by weight of a post-supercritical carbon dioxide hydroalcoholic extract of ginger;
   (B) from about 1.5% to about 2.5% by weight of the supercritical carbon dioxide extract of ginger;
   (C) from about 6% to about 8% by weight of the supercritical carbon dioxide extract of chamomile;
   (D) from about 6% to about 8% by weight of the supercritical carbon dioxide extract of hops;
   (E) from about 20% to about 24% by weight of the hydroalcoholic extract of holy basil;
   (F) from about 2.5% to about 3.5% by weight of the supercritical extract of valerian;
   (G) from about 11% to about 15% by weight of the supercritical extract of melissa;

(H) from about 13% to about 17% by weight of the hydroalcoholic extract of turmeric;

(I) from about 13% to about 17% by weight of the hydroalcoholic extract of scutellaria baicalensis;

(J) from about 3% to about 4% by weight of the hydroalcoholic extract of chamomile; and (K) from about 3% to about 4%, by weight of the hydroalcoholic extract of hops.

4. A composition according to claim 1, wherein the composition comprises the post-supercritical carbon dioxide hydroalcoholic extract of ginger and the supercritical carbon dioxide extract of ginger at a weight ratio of from about 4 to about 5 parts of post-supercritical carbon dioxide hydroalcoholic extract per 1 part of supercritical carbon dioxide extract.

5. A composition according to claim 1, wherein the composition comprises the supercritical carbon dioxide extract of chamomile and the hydroalcoholic extract of chamomile in a weight ratio of from about 1.75 to about 2.25 parts of the supercritical carbon dioxide extract per 1.0 part of the hydroalcoholic extract.

6. A composition according to claim 1, wherein the composition comprises the supercritical carbon dioxide extract of hops and the hydroalcoholic extract of hops in a weight ratio of from about 1.75 to about 2.25 parts of the supercritical carbon dioxide extract per 1.0 part of the hydroalcoholic extract.

7. A composition according to claim 1, wherein the post-supercritical carbon dioxide hydroalcoholic extract of ginger comprises from about 2% to about 4% by weight of pungent compounds.

8. A composition according to claim 1, wherein the supercritical carbon dioxide extract of ginger comprises from about 20% to about 40% by weight of pungent compounds and from about 7% to about 9% by weight of zingiberene.

9. A composition according to claim 1, wherein the supercritical carbon dioxide extract of valerian comprises from about 50% to about 70% by weight of valepotriates.

10. A composition according to claim 1, wherein the supercritical carbon dioxide extract of melissa comprises from about 0.5% to about 2.0% by weight of essential oil.

11. A composition according to claim 1, wherein the supercritical carbon dioxide extract of chamomile comprises at least about 25% by weight of alpha-bisabolol.

12. A composition according to claim 1, wherein the hydroalcoholic extract of chamomile comprises at least about 3% by weight of apigeninglycosides.

13. A composition according to claim 1, wherein the supercritical carbon dioxide extract of hops comprises from about 30% to about 40% by weight of humulones, and from about 9% to about 15% by weight of lupulones.

14. A composition according to claim 1, wherein the hydroalcoholic extract of hops comprises from about 1% to about 2% by weight of xanthohumol.

15. A composition according to claim 1, wherein the hydroalcoholic extract of holy basil comprises from about 1% to about 3% by weight of ursolic acid.

16. A composition according to claim 1, wherein the hydroalcoholic extract of turmeric comprises from about 5% to about 9% by weight of curcumin.

17. A composition according to claim 1, wherein the composition comprises:

(A) from about 7% to about 11% by weight of the post-supercritical carbon dioxide hydroalcoholic extract of ginger, wherein the extract comprises from about 2% to about 4% by weight of pungent compounds;

(B) from about 1% to about 3% by weight of the supercritical carbon dioxide extract of ginger, wherein the extract comprises from about 20% to about 40% by weight of pungent compounds and from about 7% to about 9% by weight of zingiberene;

(C) from about 5.5% to about 8.5% by weight of the supercritical carbon dioxide extract of chamomile, wherein the extract comprises at least about 25% by weight of alpha-bisabolol;

(D) from about 5.5% to about 8.5% by weight of the supercritical carbon dioxide extract of hops, wherein the extract comprises from about 30% to about 40% by weight of humulones, and from about 9% to about 15% by weight of lupulones;

(E) from about 18% to about 26% by weight of the hydroalcoholic extract of holy basil, wherein the extract comprises from about 1% to about 3% by weight of ursolic acid;

(F) from about 2.0% to about 4.0% by weight of the supercritical carbon dioxide extract of valerian, wherein the extract comprises from about 50% to about 70% by weight of valepotriates;

(G) from about 10% to about 16% by weight of the supercritical carbon dioxide extract of melissa, wherein the extract comprises from about 0.5% to about 2% by weight of essential oil;

(H) from about 12% to about 18% by weight of the hydroalcoholic extract of turmeric, wherein the extract comprises from about 5% to about 9% by weight of curcumin;

(I) from about 12% to about 18% by weight of the hydroalcoholic extract of scutellaria baicalensis;

(J) from about 2.5% to about 4.5% by weight of the hydroalcoholic extract of chamomile, wherein the extract comprises at least about 3% by weight of apigeninglycosides; and (K) from about 2.5% to about 4.5% by weight of the hydroalcoholic extract of hops, wherein the extract comprises from about 1% to about 2% by weight of xanthohumol;

further wherein the composition comprises: (i) the post-supercritical carbon dioxide hydroalcoholic extract of ginger and the supercritical carbon dioxide extract of ginger at a weight ratio of from about 4 to about 5 parts of post-supercritical carbon dioxide hydroalcoholic extract per 1 part of supercritical carbon dioxide extract; (ii) the supercritical carbon dioxide extract of chamomile and the hydroalcoholic extract of chamomile in a weight ratio of from about 1.75 to about 2.25 parts of the supercritical carbon dioxide extract per 1.0 part of the hydroalcoholic extract, and (ii) the supercritical carbon dioxide extract of hops and the hydroalcoholic extract of hops in a weight ratio of from about 1.75 to about 2.25 parts of the supercritical carbon dioxide extract per 1.0 part of the hydroalcoholic extract.

18. A method for reducing inflammation in an animal suffering from inflammation while also promoting sleep for the animal, comprising the steps of:

(1) providing the composition of claim 1; and (2) orally administering the composition to the animal in an amount and for a time period sufficient to reduce the inflammation.

19. A method according to claim 18, wherein step (2) comprises orally administering the composition to a human.

20. A method according to claim 19, wherein the composition provided in step (1) comprises:

(A) from about 7% to about 11% by weight of the post-supercritical carbon dioxide hydroalcoholic extract of ginger;

(B) from about 1% to about 3% by weight of the supercritical carbon dioxide extract of ginger;

(C) from about 5.5% to about 8.5% by weight of the supercritical carbon dioxide extract of chamomile;

(D) from about 5.5% to about 8.5% by weight of the supercritical carbon dioxide extract of hops;

(E) from about 18% to about 26% by weight of the hydroalcoholic extract of holy basil;

(F) from about 2.0% to about 4.0% by weight of the supercritical extract of valerian;

(G) from about 10% to about 16% by weight of the supercritical extract of melissa;

(H) from about 12% to about 18% by weight of the hydroalcoholic extract of turmeric;

(I) from about 12% to about 18% by weight of the hydroalcoholic extract of scutellaria baicalensis;

(J) from about 2.5% to about 4.5% by weight of the hydroalcoholic extract of chamomile; and (K) from about 2.5% to about 4.5% by weight of the hydroalcoholic extract of hops.

21. A method according to claim 19, wherein the composition provided in step (1) comprises:

(A) from about 8% to about 10% by weight of a post-supercritical carbon dioxide hydroalcoholic extract of ginger;

(B) from about 1.5% to about 2.5% by weight of a supercritical carbon dioxide extract of ginger;

(C) from about 6% to about 8% by weight of a supercritical carbon dioxide extract of chamomile;

(D) from about 6% to about 8% by weight of a supercritical carbon dioxide extract of hops;

(E) from about 20% to about 24% by weight of the hydroalcoholic extract of holy basil;

(F) from about 2.5% to about 3.5% by weight of the supercritical extract of valerian;

(G) from about 11% to about 15% by weight of the supercritical extract of melissa;

(H) from about 13% to about 17% by weight of the hydroalcoholic extract of turmeric;

(I) from about 13% to about 17% by weight of the hydroalcoholic extract of scutellaria baicalensis;

(J) from about 3% to about 4% by weight of the hydroalcoholic extract of chamomile; and (K) from about 3% to about 4%, by weight of the hydroalcoholic extract of hops.

22. A method according to claim 19, wherein the composition provided in step (1) comprises the post-supercritical carbon dioxide hydroalcoholic extract of ginger and the supercritical carbon dioxide extract of ginger at a weight ratio of from about 4 to about 5 parts of post-supercritical carbon dioxide hydroalcoholic extract per 1 part of supercritical carbon dioxide extract.

23. A method according to claim 19, wherein the composition provided in step (1) comprises the supercritical carbon dioxide extract of chamomile and the hydroalcoholic extract of chamomile in a weight ratio of from about 1.75 to about 2.25 parts of the supercritical carbon dioxide extract per 1.0 part of the aqueous-alcoholic extract.

24. A method according to claim 19, wherein the composition provided in step (1) comprises the supercritical carbon dioxide extract of hops and the hydroalcoholic extract of hops in a weight ratio of from about 1.75 to about 2.25 parts of the supercritical carbon dioxide extract per 1.0 part of the hydroalcoholic extract.

25. A method according to claim 19, wherein, in the composition provided in step (1), the post-supercritical carbon dioxide hydroalcoholic extract of ginger comprises from about 2% to about 4% by weight of pungent compounds.

26. A method according to claim 19, wherein, in the composition provided in step (1), the supercritical carbon dioxide extract of ginger comprises from about 20% to about 40% by weight of pungent compounds and from about 7% to about 9% by weight of zingiberene.

27. A method according to claim 19, wherein, in the composition provided in step (1), the supercritical carbon dioxide extract of chamomile comprises a minimum of about 25% by weight of alpha-bisabolol.

28. A method according to claim 19, wherein, in the composition provided in step (1), the hydroalcoholic extract of chamomile comprises at least about 3% by weight of apigeninglycosides.

29. A method according to claim 19, wherein, in the composition provided in step (1), the supercritical carbon dioxide extract of hops comprises from about 30% to about 40% by weight of humulones, and from about 9% to about 15% by weight of lupulones.

30. A method according to claim 19, wherein, in the composition provided in step (1), the hydroalcoholic extract of hops comprises from about 1% to about 2% by weight of xanthohumol.

31. A method according to claim 19, wherein, in the composition provided in step (1), the hydroalcoholic extract of holy basil comprises from about 1% to about 3% by weight of ursolic acid.

32. A method according to claim 19, wherein, in the composition provided in step (1), the supercritical carbon dioxide extract of valerian comprises from about 50% to about 70% by weight of valepotriates.

33. A method according to claim 19, wherein, in the composition provided in step (1), the supercritical carbon dioxide extract of melissa comprises from about 0.5 to about 2% by weight of essential oil.

34. A method according to claim 19, wherein, in the composition provided in step (1), the hydroalcoholic extract of turmeric comprises from about 5% to about 9% by weight of curcumin.

35. A method according to claim 19, wherein the composition provided in step (1) comprises:

(A) from about 7% to about 11% by weight of the post-supercritical carbon dioxide hydroalcoholic extract of ginger, wherein the extract comprises from about 4% to about 6% by weight of pungent compounds;

(B) from about 1% to about 3% by weight of the supercritical carbon dioxide extract of ginger, wherein the extract comprises from about 20% to about 40% by weight of pungent compounds and from about 7% to about 9% by weight of zingiberene;

(C) from about 5.5% to about 8.5% by weight of the supercritical carbon dioxide extract of chamomile, wherein the extract comprises at least about 25% by weight of alpha-bisabolol;

(D) from about 5.5% to about 8.5% by weight of the supercritical carbon dioxide extract of hops, wherein the extract comprises from about 30% to about 40% by weight of humulone, and from about 9% to about 15% by weight of lupulones;

(E) from about 18% to about 26% by weight of the hydroalcoholic extract of holy basil, wherein the extract comprises from about 1% to about 3% by weight of ursolic acid;

(F) from about 2.0% to about 4.0% by weight of the supercritical extract of valerian, wherein the extract comprises from about 50% to about 70% by weight of valepotriates;

(G) from about 10% to about 16% by weight of the supercritical extract of melissa, wherein the extract comprises from about 0.5 to about 2% by weight of essential oil;

(H) from about 12% to about 18% by weight of the hydroalcoholic extract of turmeric, wherein the extract comprises from about 5% to about 9% by weight of curcumin;

(I) from about 12% to about 18% by weight of the hydroalcoholic extract of scutellaria baicalensis;

(J) from about 2.5% to about 4.5% by weight of the hydroalcoholic extract of chamomile, wherein the extract comprises at least about 3% by weight of apigeninglycosides; and (K) from about 2.5% to about 4.5% by weight of the hydroalcoholic extract of hops, wherein the extract comprises from about 1% to about 2% by weight of xanthohumol;

further wherein the composition comprises: (i) the post-supercritical carbon dioxide hydroalcoholic extract of ginger and the supercritical carbon dioxide extract of ginger at a weight ratio of from about 4 to about 5 parts of post-supercritical carbon dioxide hydroalcoholic extract per 1 part of supercritical carbon dioxide extract; (ii) the supercritical carbon dioxide extract of chamomile and the hydroalcoholic extract of chamomile in a weight ratio of from about 1.75 to about 2.25 parts of the supercritical carbon dioxide extract per 1.0 part of the hydroalcoholic extract, and (iii) the supercritical carbon dioxide extract of hops and the hydroalcoholic extract of hops in a weight ratio of from about 1.75 to about 2.25 parts of the supercritical carbon dioxide extract per 1.0 part of the hydroalcoholic extract.

36. A method according to claim 19, wherein step (2) comprises orally administering the composition in a daily dosage of at least about 500 mg.

37. A method according to claim 19, wherein step (2) comprises orally administering the composition on a daily basis for at least 4 weeks.

* * * * *